United States Patent
Aronoff-Spencer et al.

(10) Patent No.: US 12,036,003 B2
(45) Date of Patent: Jul. 16, 2024

(54) MULTIMODAL BIOMETRIC DEVICE

(71) Applicant: THE REGENTS OF THE UNIVERSITY OF CALIFORNIA, Oakland, CA (US)

(72) Inventors: Eliah Aronoff-Spencer, San Diego, CA (US); Tom Kalisky, La Jolla, CA (US); Daniel Johnson, Escondido, CA (US); Alex Grant, San Diego, CA (US); Steve Saggese, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 303 days.

(21) Appl. No.: 17/416,319

(22) PCT Filed: Dec. 20, 2019

(86) PCT No.: PCT/US2019/068166
§ 371 (c)(1),
(2) Date: Jun. 18, 2021

(87) PCT Pub. No.: WO2020/132645
PCT Pub. Date: Jun. 25, 2020

(65) Prior Publication Data
US 2022/0071489 A1    Mar. 10, 2022

Related U.S. Application Data

(60) Provisional application No. 62/783,156, filed on Dec. 20, 2018.

(51) Int. Cl.
*A61B 5/01*    (2006.01)
*A61B 5/00*    (2006.01)
(Continued)

(52) U.S. Cl.
CPC ............. *A61B 5/01* (2013.01); *A61B 5/0033* (2013.01); *G06V 10/143* (2022.01);
(Continued)

(58) Field of Classification Search
CPC ........ A61B 5/01; A61B 5/0033; A61B 5/0077; A61B 5/02444; A61B 5/0245;
(Continued)

(56) References Cited

U.S. PATENT DOCUMENTS

| | | | |
|---|---|---|---|
| 6,504,945 B1 * | 1/2003 | Helot | G06V 40/13 382/126 |
| 6,687,391 B1 * | 2/2004 | Scott | G06V 40/1335 382/126 |

(Continued)

FOREIGN PATENT DOCUMENTS

| | | | | |
|---|---|---|---|---|
| CN | 110414354 | 11/2019 | | |
| EP | 2709037 A2 * | 3/2014 | | A47B 81/00 |

OTHER PUBLICATIONS

Saggese et al., "Biometric recognition of newborns and infants by non-contact fingerprinting: lessions learned [version 2; peer review: 3 approved]," Gates Open Research 2019, 3:1477, May 29, 2019, 25 pages.

International Search Report and Written Opinion mailed Mar. 3, 2020 for International Application No. PCT/US2019/068166.

*Primary Examiner* — John B Strege
(74) *Attorney, Agent, or Firm* — Dorsey & Whitney LLP

(57) ABSTRACT

A multimodal biometric device is disclosed. An apparatus may include a non-contact imaging system. The non-contact imaging system may include imaging optics, optical illumination optically coupled to the imaging optics, and a configurable body part support to support different body parts at corresponding focal lengths to capture different portions of the different body parts. An apparatus may also include a (Continued)

602

Small Finger Aperture
604

Large Finger Aperture
606 housing coupled to the imaging optics, the optical illumination, and the configurable body part support.

12 Claims, 20 Drawing Sheets

(51) Int. Cl.
| | | |
|---|---|---|
| *G06V 10/143* | (2022.01) | |
| *G06V 10/147* | (2022.01) | |
| *G06V 40/10* | (2022.01) | |
| *G06V 40/12* | (2022.01) | |
| *G06V 40/13* | (2022.01) | |
| *G06V 40/40* | (2022.01) | |
| *G06V 40/70* | (2022.01) | |

(52) U.S. Cl.
CPC ........ *G06V 10/147* (2022.01); *G06V 40/1312* (2022.01); *G06V 40/1347* (2022.01); *G06V 40/1382* (2022.01); *G06V 40/45* (2022.01); *G06V 40/70* (2022.01); *G06V 40/15* (2022.01)

(58) Field of Classification Search
CPC .............. A61B 5/1172; A61B 5/14542; G06V 10/143; G06V 10/147; G06V 10/1312; G06V 10/1347; G06V 10/1382; G06V 40/45; G06V 40/70; G06V 40/15
See application file for complete search history.

(56) References Cited

U.S. PATENT DOCUMENTS

| | | | |
|---|---|---|---|
| 7,728,959 B2 | 6/2010 | Waldman et al. | |
| 2006/0115132 A1 | 6/2006 | Schneider et al. | |
| 2010/0182126 A1* | 7/2010 | Martis ................. | A61B 5/1172 340/5.82 |
| 2011/0235872 A1 | 9/2011 | Rowe et al. | |
| 2012/0075442 A1* | 3/2012 | Vujic ..................... | G07C 9/257 235/472.01 |
| 2012/0177257 A1* | 7/2012 | Maev ................... | A61B 5/1172 382/124 |
| 2015/0086090 A1* | 3/2015 | Jung ................. | G06V 40/1365 382/124 |
| 2015/0220772 A1 | 8/2015 | Mil'shtein et al. | |
| 2018/0253588 A1 | 9/2018 | Aronoff-Spencer et al. | |
| 2018/0260603 A1 | 9/2018 | Aronoff-Spencer et al. | |
| 2020/0202101 A1* | 6/2020 | Howell ............. | G06V 40/1312 |

* cited by examiner

MULTIMODAL BIOMETRIC DEVICE

CROSS-REFERENCE TO RELATED APPLICATION

The present application is a U.S. national phase of PCT International Patent Application No. PCT/US2019/068166, filed Dec. 20, 2019 and titled "RESISTIVE POLYMER MEMBRANES FOR ENERGY STORAGE DEVICES," which claims priority to U.S. Provisional Patent Application No. 62/783,156, filed on Dec. 20, 2018, the content of which are incorporated herein in their entirety.

STATEMENT REGARDING FEDERALLY SPONSORED R&D

This invention was made with government support under Grant No. OPP1131841, awarded by Bill & Melinda Gates Foundation. The government has certain rights in the Invention.

TECHNICAL FIELD

Various embodiments generally relate to a biometric device. More particularly, various embodiments relate to a multimodal biometric device.

BRIEF SUMMARY OF EMBODIMENTS

Embodiments of the disclosure are directed to a multimodal biometric device. In embodiments, an apparatus may include a non-contact imaging system. The non-contact imaging system may include imaging optics. The non-contact imaging system may also include optical illumination optically coupled to the imaging optics. The non-contact imaging system may further include a configurable body part support to support different body parts at corresponding focal lengths to capture different portions of the different body parts. The configurable body part support may include a configurable aperture configurable to different geometries to accommodate the different portions of the different body parts. An apparatus may also include a housing coupled to the imaging optics, the optical illumination, and the configurable body part support.

In embodiments, the configurable body part support may include interchangeable supports couplable to and decouplable from the housing. Each one of the interchangeable supports may support one of the different body parts at one of the corresponding focal lengths. Each one of the interchangeable supports may include one of the different geometries for the configurable aperture.

In embodiments, the configurable body part support may include selectable supports integrated into the housing. Each one of the selectable supports may support one of the different body parts at one of the corresponding focal lengths. Each one of the selectable supports may include one of the different geometries for the configurable aperture. The configurable body part may also include a selection mechanism coupled to the selectable supports and the housing. Based on user input via the selection mechanism, one of the selectable supports may be selected.

In embodiments, the configurable aperture may include adjustable edges to configure the configurable aperture into one of the different geometries.

In embodiments, one of the different body parts may include one or more fingers, a palm pad, a palm, and a ball of a foot.

In embodiments, the configurable body part support may include one of a rotary dial and a linear slide.

In embodiments, the configurable body part support may block ambient external light from the non-contact imaging system during imaging of a portion of interest.

In embodiments, the non-contact imaging system may capture images at a resolution of at least 1000 pixels-per-inch.

In embodiments, the non-contact imaging system may include one or more cameras.

In embodiments, the non-contact imaging system may include one or more of a CMOS and CCD imager. The non-contact imaging system may be monochromatic or color detecting.

In embodiments, the imaging optics may include a fixed focus and a fixed focal length or an adjustable focus and an adjustable focal length.

In embodiments, the optical illumination may include one or more colors of LEDs over a range of wavelengths from UV through NIR.

In embodiments, the apparatus may further include imagers. The apparatus may further include illumination. The imagers and the illumination may collect additional types of biometric images.

In embodiments, a portion of interest accommodated by the configurable aperture may expose a portion of interest to the imaging optics and the optical illumination to provide non-contact imaging of the portion of interest.

In embodiments, health parameters of a subject may be measured using the non-contact imaging system, the imaging optics, and the optical illumination.

In some embodiments, an apparatus is disclosed. An apparatus may include a non-contact imaging system. The non-contact imaging system may include imaging optics. The non-contact imaging system may also include optical illumination optically coupled to the imaging optics. The non-contact imaging system may further include a configurable body part support to support different body parts at corresponding focal lengths to capture different portions of the different body parts. The configurable body part support may include a configurable aperture configurable to different geometries to accommodate the different portions of the different body parts. A portion of interest accommodated by the configurable aperture may expose the portion of interest to the imaging optics and the optical illumination to provide non-contact imaging of the portion of interest. An apparatus may also include a housing coupled to the imaging optics, the optical illumination, and the configurable body part support such that the non-contact imaging system, the portion of interest accommodated by the configurable aperture, and the housing may enclose the imaging optics and the optical illumination. An apparatus may further include a contact-based system to collect biometric data from additional body parts.

In embodiments, the configurable body part support may include interchangeable supports couplable to and decouplable from the housing. Each one of the interchangeable supports may support one of the different body parts at one of the corresponding focal lengths. Each one of the interchangeable supports may include one of the different geometries for the configurable aperture.

In embodiments, the configurable body part support may include selectable supports integrated into the housing. Each one of the selectable supports may support one of the different body parts at one of the corresponding focal lengths. Each one of the selectable supports may include one of the different geometries for the configurable aperture. The configurable body part support may also include a selection mechanism coupled to the selectable supports and the housing. Based on user input via the selection mechanism, one of the selectable supports may be selected.

In embodiments, the configurable aperture may include adjustable edges to configure the configurable aperture into one of the different geometries.

In embodiments, the configurable aperture may support the body part except the portion of interest.

In embodiments, friction ridges of one of the different body parts may be imaged for minutiae-based biometrics.

In embodiments, the imaging system and the contact-based system may share optical components.

In embodiments, the imaging system and the contact-based system may be based on one of frustrated total internal reflection (FTIR) and direct contact viewing with a platen.

In embodiments, the imaging system and the contact-based system may be independent subsystems that are located within the housing In embodiments, the contact-based system may be based on one of frustrated total internal reflection (FTIR), direct contact imaging with a platen, capacitive imaging, and ultrasonic imaging.

In embodiments, the configurable body part support may include one of a rotary dial and a linear slide.

In embodiments, the imaging system may capture images at a resolution of at least 1000 pixels-per-inch.

In embodiments, the imaging system may include one of a CMOS and CCD imager. The non-contact imaging system may be monochromatic or color detecting.

In embodiments, the optical illumination may include one or more colors of LEDs over a range of wavelengths from UV through NIR.

In embodiments, health parameters of a subject may be measured using one or more of the imaging system, the imaging optics, and the optical illumination.

In some embodiments, an apparatus for collecting images of a body part for biometric identification for different subject ages is disclosed. An apparatus may include a non-contact imaging system. An apparatus may also include imaging optics. An apparatus may also include optical illumination coupled to the imaging optics. An apparatus may further include a body part support that may support the body part at a field of view and focus location of the non-contact imaging system. The body part support may include multiple open apertures to receive different surfaces of different body parts to be imaged. The multiple open apertures may be characterized by one or more of a different size and a different shape to support different body parts for different-aged subjects. The multiple open apertures may support the different body parts along multiple edges of the different surfaces of the different body parts to be imaged. The different surfaces of the different body parts may be directly exposed to the non-contact imaging system during imaging. Friction ridges on the different surfaces of the different body parts may be imaged for minutiae-based biometrics. An apparatus may further include a housing coupled to the imaging optics, the optical illumination, and the body part support. The housing may surround the non-contact imaging system, the imaging optics, the optical illumination, and the body part support.

In embodiments, the multiple open apertures may be integrated with the housing. The multiple open apertures may include adjustable edges to accommodate the different surfaces of the different body parts.

In embodiments, the body part support may include different sized apertures removable from and attachable to the housing.

In embodiments, a method may include capturing a first fingerprint using a fingerprint capture device. The fingerprint capture device may include an imaging system. The imaging system may include imaging optics. The imaging system may also include optical illumination optically coupled to the imaging optics. The fingerprint capture device may further include a configurable body part support to support different body parts at corresponding focal lengths to capture different portions of the different body parts. The configurable body part support may include a configurable aperture configurable to different geometries to accommodate the different portions of the different body parts. A portion of interest accommodated by the configurable aperture may expose the portion of interest to the imaging optics and the optical illumination to provide non-contact imaging of the portion of interest. The fingerprint capture device may also include a housing coupled to the imaging optics, the optical illumination, and the configurable body part support such that the non-contact imaging system, the portion of interest accommodated by the configurable aperture, and the housing may enclose the imaging optics and the optical illumination. The method may include capturing a second fingerprint using the fingerprint capturing device.

In some embodiments, the second fingerprint may be captured using a contact-based imaging system. The contact-based imaging system may be based on one of frustrated total internal reflection (FTIR), direct contact imaging with a platen, capacitive imaging, and ultrasonic imaging.

BRIEF DESCRIPTION OF THE DRAWINGS

The technology disclosed herein, in accordance with one or more various embodiments, is described in detail with reference to the following figures. The drawings are provided for purposes of illustration and merely depict example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

Figure 1:
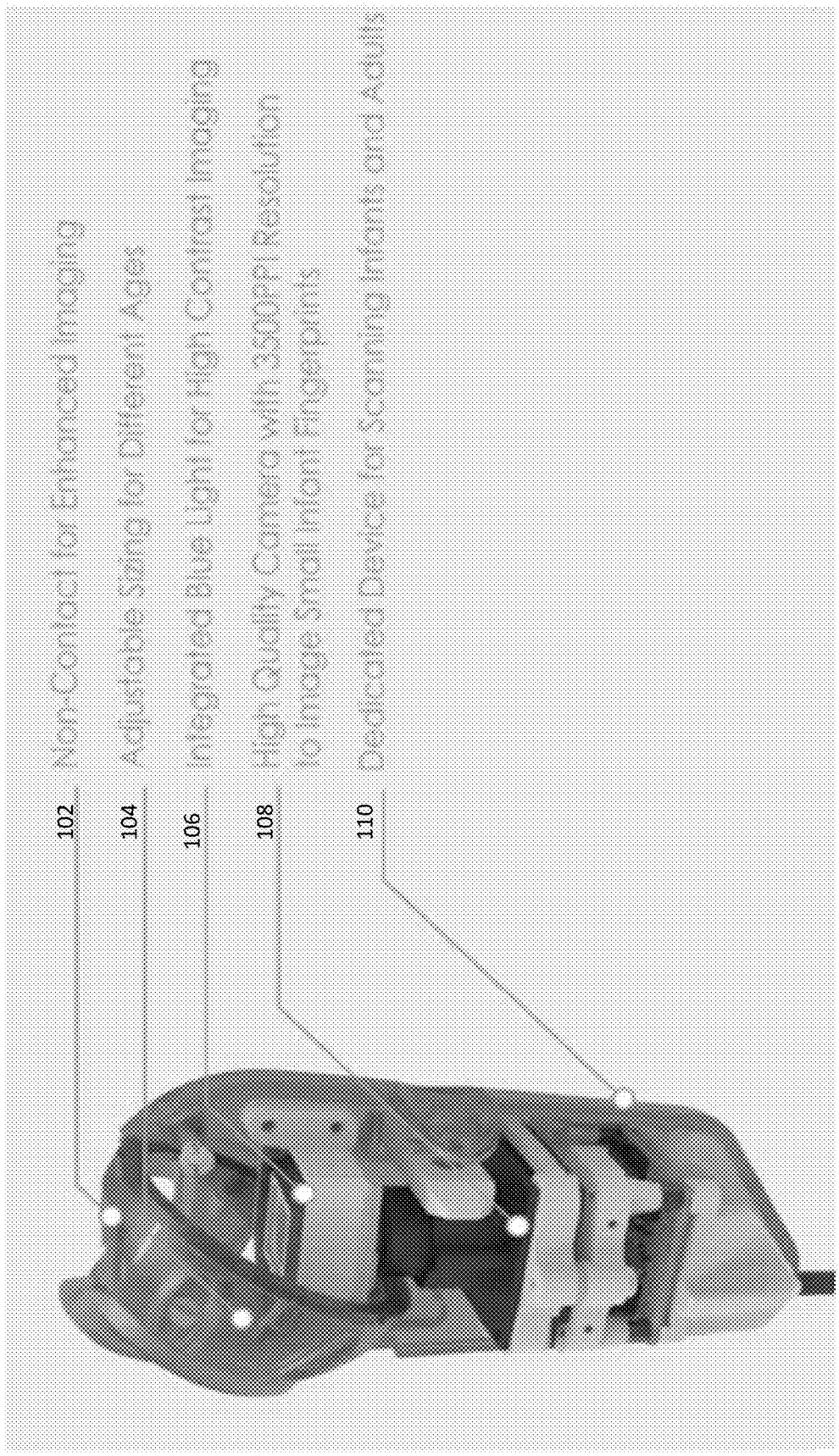
FIG. 1 illustrates an example device, in accordance with various embodiments of the present disclosure.

The figures are not intended to be exhaustive or to limit the presently disclosed technology to the precise form disclosed. It should be understood that the presently disclosed technology can be practiced with modification and alteration, and that the disclosed technology be limited by the claims and the equivalents thereof.

DETAILED DESCRIPTION OF THE EMBODIMENTS

Existing biometric identification technologies may include optical sensors, capacitive scanners, and ultrasound/ultrasonic sensors. Optical sensors may capture the image of fingerprints using a contact method called frustrated total internal reflection (FTIR). This is the most common type of fingerprint sensor. Capacitive scanners may use a pixel array of capacitors, instead of visible light, to produce an image of fingerprints. This is a contact method. Ultrasonic scanners may use ultrasonic sound waves to read patterns of fingerprints. Ultrasonic sound waves reflected from the fingertip surface may be measured by the sensor and a fingerprint pattern image may be produced. This is a contact method. Other systems may use software to obtain an image of the print from different devices, such as cellphones. These systems are not capable of properly capturing biometrics from infants.

Infants have both physical and behavioral differences from adults that impact the ability to obtain a high-quality fingerprint. Infant fingerprints are fully formed at birth, but they are approximately four to five times smaller than those of adults. Existing fingerprint devices typically obtain fingerprint images at a resolution of 500 to 1000 pixels-per-inch (PPI). This resolution may be sufficient to resolve features on adult fingerprints which have friction ridge-to-ridge distances of about 0.5 mm, but may be inadequate for infants that can have friction ridge-to-ridge distances as small as 0.125 mm. While some existing fingerprint devices may be modified to increase the resolution so that these smaller details of an infant can be resolved, this fails to solve all of the issues associated with obtaining fingerprints from infants. For example, an adult can gently place their finger onto the surface of the device and keep contact with little distortion. Infants, on the other hand, need to be helped through the process and may exhibit behaviors that are not helpful, such as an inability to place a finger flat onto the device for contact imaging, or an inability to stay motionless and properly aligned for non-contact methods. Infants may exhibit involuntary finger curling and whole hand grasping due to the palmar grasp reflex, making alignment of the finger difficult and often resulting in motion blur. In addition, infant skin is softer and more pliable than the skin of adults, which creates issues with contact-based scanners.

For example, the infant fingerprint may flatten against the surface of an imager and the small ridge features of the infant will collapse together leading to fusion of features that cannot be resolved by any fingerprint method operating at 500-1000 PPI. For contact methods, the grasp reflex of an infant is problematic and will cause the finger to react inconsistently. A single portion of the finger will typically contact the fingerprinting platen first, then the remaining portions of the print will contact as the finger is put into place. Invariably, the finger does not go down the same way each time and the print may be distorted due to the skin pliability. For non-contact methods, this infant grasping behavior requires the hand of the infant to be held open and the fingers held flat so that the fingerprint can be viewed. This often requires multiple practitioners to hold the infant hand and fingers while the free-space camera is operated, making the interaction difficult.

Another concern with fingerprinting infants may be that their finger size is highly variable between infants and it changes over time. For a given infant, the finger size and the feature size will increase until about 15 years of age, where the finger size and the print features may stabilize to the adult levels. Thus, devices must accommodate the range of physical sizes of the infant and account for growth of an individual's fingerprint over time so that fingerprint templates can be compared over time. As the child grows, the appropriate technology used to obtain the biometric may change since the issues with infants will often reduce with time. For example, the palmar grasp reflex will no longer occur around 12 months of age and the child is more capable of placing a finger onto a device under direction. As they age, the prints also become firmer, thus allowing for the potential use of contact printers as the child ages. The presently disclosed technology provides a device that may collect various features of body parts across all ages.

Disclosed are devices, apparatuses, components, configurations, methods, systems, and designs that enable and pertain to a portable, multimodal biometric capture device, that may be used for the collection of fingerprints and other biometrics for all ages, starting at birth. The presently disclosed technology works with computing devices. In an embodiment, the multimodal biometric capture device may include a non-contact imaging system. For example, a non-contact imaging system may ensure that the pliable infant skin does not come in contact with a surface or platen that deforms the fingerprint.

The non-contact imaging system may be non-deforming while capturing fingerprints using a high-resolution, free-space imager with controlled interaction and lighting to obtain accurate detailed minutiae for identification/verification of the infant from birth and as the infant ages. It should be appreciated that deformation of the fingerprint through existing imaging systems may lead to incorrect determination of minutiae locations and make longitudinal identification difficult or impossible. In some embodiments, the non-contact imaging system may include a resolution of 1000 PPI, 1500 PPI, 2000 PPI, 2500 PPI or higher resolutions. These resolutions may be used to accurately image smaller friction ridges and minutiae for identification/verification of an infant from birth.

In embodiments, an operator and a subject may use the multimodal biometric capture device. If the subject is an infant, or is unable to properly place their finger on the device, the operator may select a configurable aperture based on the finger size, place the finger in the selected aperture, trigger the camera, and collect the finger image. The configurable aperture may be configurable to allow the finger to be positioned such that the fingerprint of the finger may be exposed to the contactless camera underneath to properly image the fingerprint. The configurable aperture may be reconfigured as appropriate for different portions of different body parts. The configurable aperture may allow the finger to be placed on the device reproducibly at a distance from the camera based on a focal distance, field of view, and other capture parameters. The configurable aperture may be configurable to different geometries to accommodate different portions of the different body parts. For example, the configurable aperture may be fingerprint shaped for a finger print (e.g., an oval-like aperture) ear-shaped for an ear (e.g., a bigger more circular aperture), and palm-pad-shaped (e.g., potentially more rectangular of an aperture).

A configurable body part support may support the finger along a front, a bottom, and the sides of the finger; this may allow the capture component to obtain multiple features (e.g. minutiae) to identify an infant. The configurable body part support may be reconfigured as appropriate for different portions of different body parts. The configurable body part support may include a configurable aperture that may be configurable to accommodate different portions of different body parts. The configurable body part support may also provide a light shield to block out ambient light that may reduce contrast of the image. For example, ambient light may reduce contrast of the collected image.

In embodiments, the configurable aperture may include multiple apertures. Each aperture may have a different size and a different shape corresponding to a different feature, or portion, of a different body part to be collected. The multiple apertures may provide adjustability to conform to a variety of body part features. For example, the presently disclosed technology could capture each of a single newborn's various sized fingerprints, and properly support each of the various sized fingers from a single hand. In one example, eyes, feet, hands, ears, and other body parts may be imaged as well.

Additionally, the presently disclosed technology can: incorporate contact fingerprint methods to collect fingerprints of adults and for children as they reach adulthood; enable the collection of multiple types of biometrics (e.g., images of the face, eyes, ears, palms, and feet, or multimodal biometrics); and enable liveness detection and health status by incorporating a variety of sensor technologies (e.g., IR thermometer, pulse, breathing and oxygen sensors).

The presently disclosed technology may acquire non-contact images from non-compliant subjects, accommodating size variation, and motion/misplacement (e.g., swappable capture-device tops, interchangeable apertures, selectable apertures, controllable apertures or rotatable/changeable sized apertures working in concert with lighting and high resolution imaging that allows low integration times to remove motion artifacts and light inconsistencies).

The presently disclosed technology may be able to collect fingerprints and other biometrics from infants, children, and adults. Infants and children have small fingers (i.e. small fingerprints and higher density of ridges/valleys with the identifying minutiae points) where the prints are present but easily deformed by contact methods. To account for this, a high-resolution imager, as described herein, may be used to resolve the smaller details of infant prints and may be scaled appropriately so that industry standard fingerprint analysis tools can be exploited.

Infants' skin is also softer and more pliable then adults, and they may have a variability of skin conditions from peeling to very dry or wet. These issues may render the standard contact-based imaging devices inoperable. Infants are also often "uncooperative" because they are unable to reproducibly place their fingers onto a standard fingerprint scanner typically used for adults. Since infants are uncooperative (cannot place their fingers properly without assistance) and have a grasp reflex, it makes it difficult to position the finger properly without motion artifacts and/or centered on the field of view of the camera. The presently disclosed technology may obtain infant/child fingerprints with a quality that allows for identity verification or identification from birth and as they age. As the child gets older, the finger gets larger and the presently disclosed technology may be used to adjust the image so that fingerprint features are consistent. For example, the ridge frequency of the finger may be evaluated and resampled so that the ridge frequency is consistently about 7 to about 12 pixels from each ridge-to-ridge.

The presently disclosed technology may be a non-contact, non-deforming imager that captures undisturbed images at an optical resolution to obtain accurate detailed minutiae for identification. The presently disclosed technology may include a non-contact imager that allows for control of the infant finger and can accommodate different sizes of fingers on a single hand, or differences in age between subjects, from birth through old age. FIG. 1 illustrates example device 110, in accordance with various embodiments of the present disclosure. Example device 110 may include non-contact enhanced imaging 102, adjustable sizing 104 for different-sized fingers, an integrated blue light 106 for high contrast imaging, and a high quality camera 108 having a resolution from 2000 to 4000 ppi.

In embodiments, the presently disclosed technology can incorporate contact fingerprint methods to collect fingerprints of adults and for children as they reach adulthood. For example, the presently disclosed technology may include a contact-type fingerprint imaging system in the same housing as the non-contact imaging system to collect fingerprints of infants and adults. As such, fingerprint data may be collected for all age groups in a single device. The contact-based imager may include a resolution of at least 1000 PPI. For example, using multiple optical and physical configurations and contact and non-contact subassemblies in a single device, collection of contact and non-contact fingerprint images may be accomplished with the multimodal biometric capture device. In embodiments, the contact and non-contact imaging system could use the same camera and may be designed to share cameras and optics. In some embodiments, the contact and non-contact imaging system can be independent subsystems including a variety of cameras, sensors, processors, memory, and other components that are housed in a single device. In some embodiments, multiple features of a subject or of multiple subject can be collected simultaneously.

The presently disclosed technology may enable the collection of multiple types of biometrics for identification, such as the collection of images of the face, eyes, ears, palms, feet, hands, and/or other identifying features (i.e. multimodal biometrics). For example, the housing may include multiple sensor technologies (e.g., IR thermometer, pulse rate monitor, ECG, breathing and oxygen sensors) to allow for the health status of the infant to be assessed. The housing may be coupled to the imaging optics, optical illumination and the configurable body part support.

The presently disclosed technology may also enable liveness detection and health status to detect biometric information that a live person is having their fingerprint collected and that spoofing (impersonation) is not occurring. For example, proof that the actual finger of a person is being scanned would be supported by having the values of several biometric readings within normal ranges. In embodiments, the multimodal biometric capture device may include a pulse oxygenation sensor. For example, pulse oxygenation sensor may include LEDs, or other light sources, at several wavelengths to measure the oxygen saturation in the blood from the finger placed onto the device. The wavelengths may range from UV to NIR, and may extend beyond these ranges as well. In some embodiments, the multimodal biometric capture device may include an ECG sensor. For example, the integrated ECG sensor may measure the electrical activity of the heartbeat with contacts across the finger and hand. In embodiments, the multimodal biometric capture device may include a thermal IR temperature sensor. For example, the thermal IR sensor pointed at the finger can indicate that a finger in contact with the device is at near body temperature. The IR thermal sensor could also be used for obtaining an accurate body temperature, as a temporal artery body temperature measurement.

In addition to spoof detection, these readings can also be monitored for a health status. These readings can be used to determine if the person has a fever, has poor blood oxygenation, has a proper heartbeat, etc., which can be used to determine a health status. In addition, these values can be combined to determine other health biometrics, such as, for example, blood pressure. It should be appreciated that additional sensors may be added to determine additional health biometrics or improve the accuracy of the health biometrics.

The camera/lens system of the multimodal biometric capture device may be configured to obtain high resolution imagery. For example, the range of resolutions may range from 500 to 4000 PPI. The fingerprint image may be collected at high resolution, processed to enhance contrast, and produce a clean fingerprint image, then, in some embodiments, resampled to about 500 PPI so that existing fingerprint analysis software can be used to obtain a fingerprint template. For example, the images may be collected at high resolution by a monochrome CMOS imager with custom optics having a resolution and a depth of field. The multimodal biometric capture device may include an ergonomic shell for ease of use. In embodiments, the multimodal biometric capture device may include an external trigger to control image capture. In some embodiments, the exposure may be less than about 20 ms.

The multimodal biometric capture device may also include dedicated illumination to enhance the contrast of the fingerprint image. For example, the finger, or other body part, may be enclosed so that ambient light does not affect imaging. For non-contact imaging, the feature to be imaged and the multimodal biometric capture device may enclose the imaging system such that ambient light does not affect the resulting image. In embodiments, multiple colors of light and multiple polarizations may be used on the illumination and/or the detection by the camera while imaging.

The multimodal biometric capture device may use a configurable aperture to ensure proper finger placement. The configurable aperture may help align the fingers in the center of the camera field of view and support the finger along the edges with minimal interaction so that the finger stays flat. For example, infants have a grasp reflex that the configurable aperture may help reduce. The configurable aperture may have different sizes to accommodate different ages and finger sizes. As described herein, the size of the configurable aperture may vary using different techniques. For example, a configuration of the configurable aperture for a palm may be appropriate to capture a palm pad, another configuration may be appropriate to capture an iris, and another may be appropriate to capture a footprint.

In some embodiments, the presently disclosed technology may include an integrated mechanical mechanism to allow the operator to switch through a variety of predetermined fixed aperture sizes. In embodiments, presently disclosed technology may include swappable device tops. These swappable device tops may be decouplable and couplable to a housing of the presently disclosed technology. The swappable tops may be able receive different features to allow for the collection of images from fingers of different sizes and/or other features of other body parts, such as the hand, palm pad, feet, eye, ear, and the like. The swappable tops may change an overall shape of the top of the device to better facilitate the collection of prints from different subjects, such as a rounded top to allow for an infant to grasp, or shaped to accommodate other body locations. In embodiments, the presently disclosed technology may include a single aperture including adjustable edges. The edges of the aperture can be movable and may allow for the aperture exposed to the camera to be increased or decreased to account for different size fingers, for example.

Figure 16:
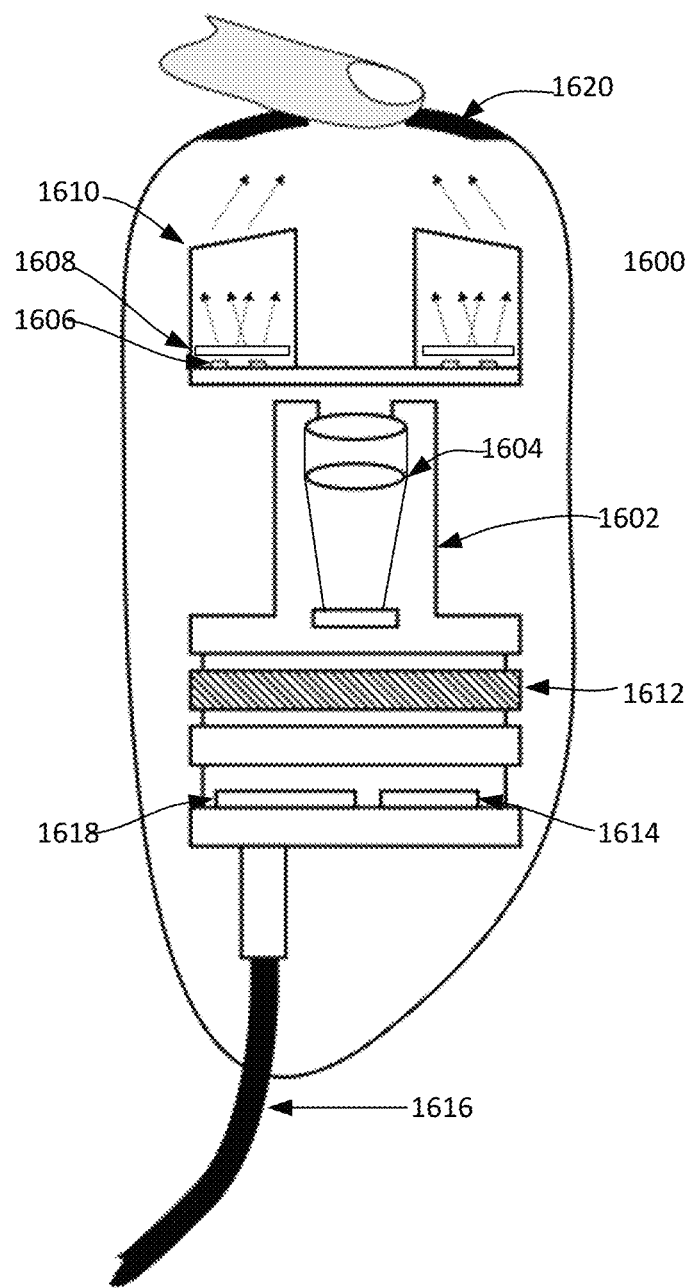
FIG. 16 illustrates an example device, in accordance with various embodiments of the present disclosure.

FIG. 16 illustrates example device 1600, in accordance with various embodiments of the present disclosure. Device 1600 may capture different features of different body parts. Device 1600 may be configured to collect images for a range of finger sizes of infants of each hand and fingers as the infant grows. Fingers, and other body parts, may be placed on configurable aperture 1622. The device housing may include camera system 1602 and optics 1604 with a focal length to image the underside of a finger in a non-contact fashion.

Camera system 1602 may include one or more of a CMOS, CCD imager, and other imagers. Camera system 1602 may be monochromatic or in color. In embodiments, optics 1604 may have a longer depth of field (i.e., greater than 10 mm) to properly image the print from, for example, the finger. Camera/lens system 1602 of the biometric capture device may be configured to obtain high resolution imagery. For example, the range of resolutions may be a range from 1500 to 5000 PPI. The device may include one or more integrated LEDs 1606 that may illuminate the finger with light to enable short integration times (<20 milliseconds). This may enable blur free images. LEDs 1606 can be of one or more wavelengths, and, depending upon the configuration desired, other optical elements can be used to polarize or diffuse the light. For example, a single color in the blue/green spectrum may be used to enable high contrast surface features of the skin. The use of a single color LED with a monochromatic camera may be used as well. In some embodiments, the LEDs may be diffused with a sheet diffuser 1608 to homogenize the light. In embodiments, a waveguide 1610 may be used to control the angle of the light to generally illuminate the finger, or other body part, indirectly at an angle to reduce specular reflections from the body part surface. The camera system 1602 and LEDs 1606 may be operatively connected to circuits 1612 to operate and control the camera, power the LEDs, control the exposure, and perform other operations. The device 1600 can include circuits 1612 to perform image enhancement and analysis with the use of a processor 1614 to evaluate the fingerprint image. Device 1600 may be operatively coupled to another device via a wired connection 1618 or a wireless connection via 1620.

Figure 17:
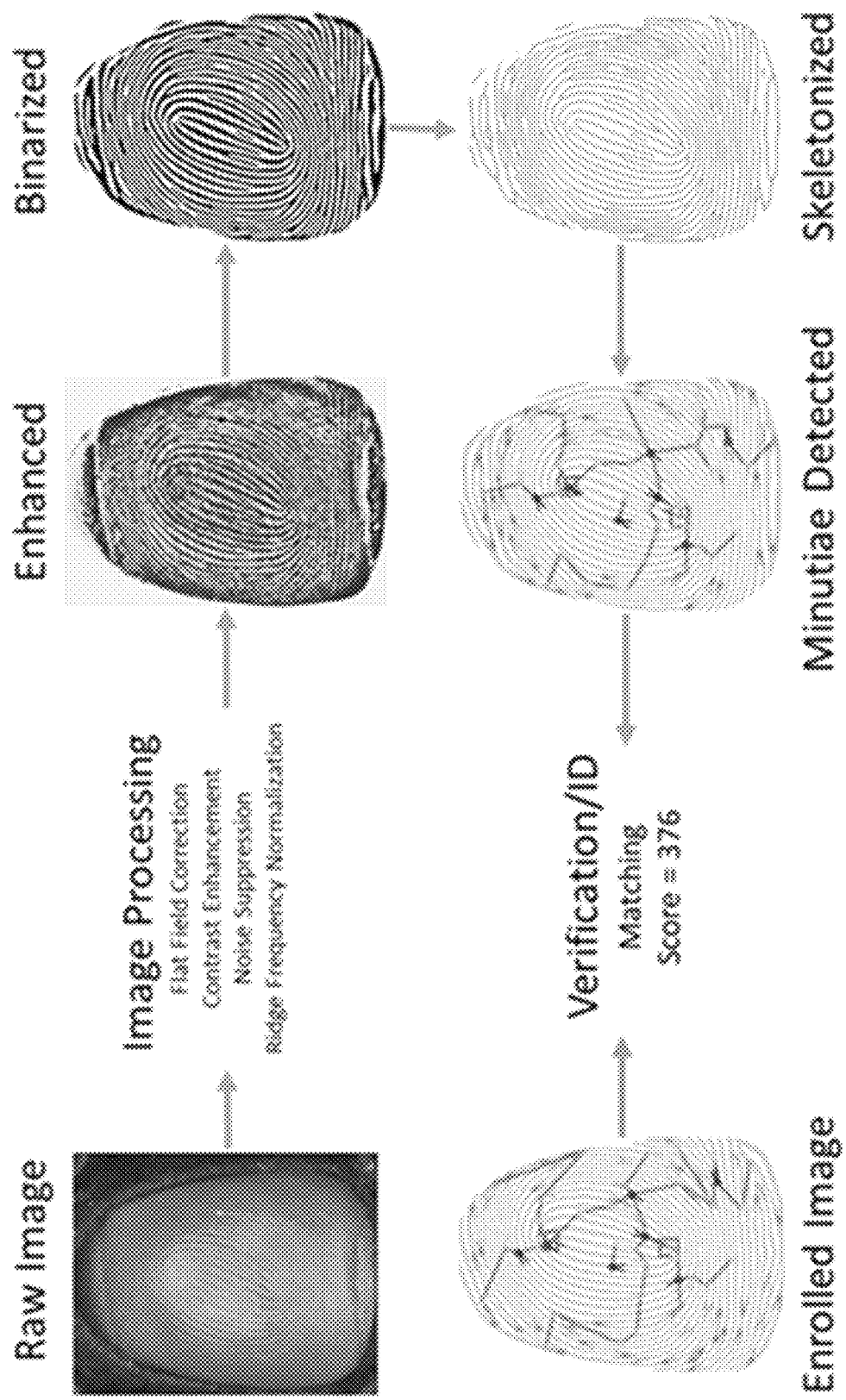
FIG. 17 illustrates example image processing conducted on the raw image collected.

FIG. 17 illustrates example image processing conducted on the raw image collected. The example image processing may accept a monochromatic 12-bit raw image, perform a flat-field correction to eliminate lighting non-uniformity, conduct a local contrast enhancement, noise suppression, and a normalization of the pixel distance from ridge-to-ridge. The manipulated/enhanced image may be resampled to a reduced pixel count with an 8-bit pixel intensity range. The resulting enhanced image may be processed to create binarized and skeletonized images, followed by minutiae detection and the creation of an interoperable, biometric template, which can then be used for verification and/or identification of a subject from previously stored templates stored from a prior enrollment. The template can be transferred to an external computer for input into an automatic biometric identification system (ABIS) via a hardwire connection, such as USB 1616, another wired connection, or a wireless connection 1618, as illustrated in FIG. 16. The system control, image processing and template creation can also be conducted on an external computer by transferring the raw imagery to the computer without any processing conducted on the device.

Figure 18:
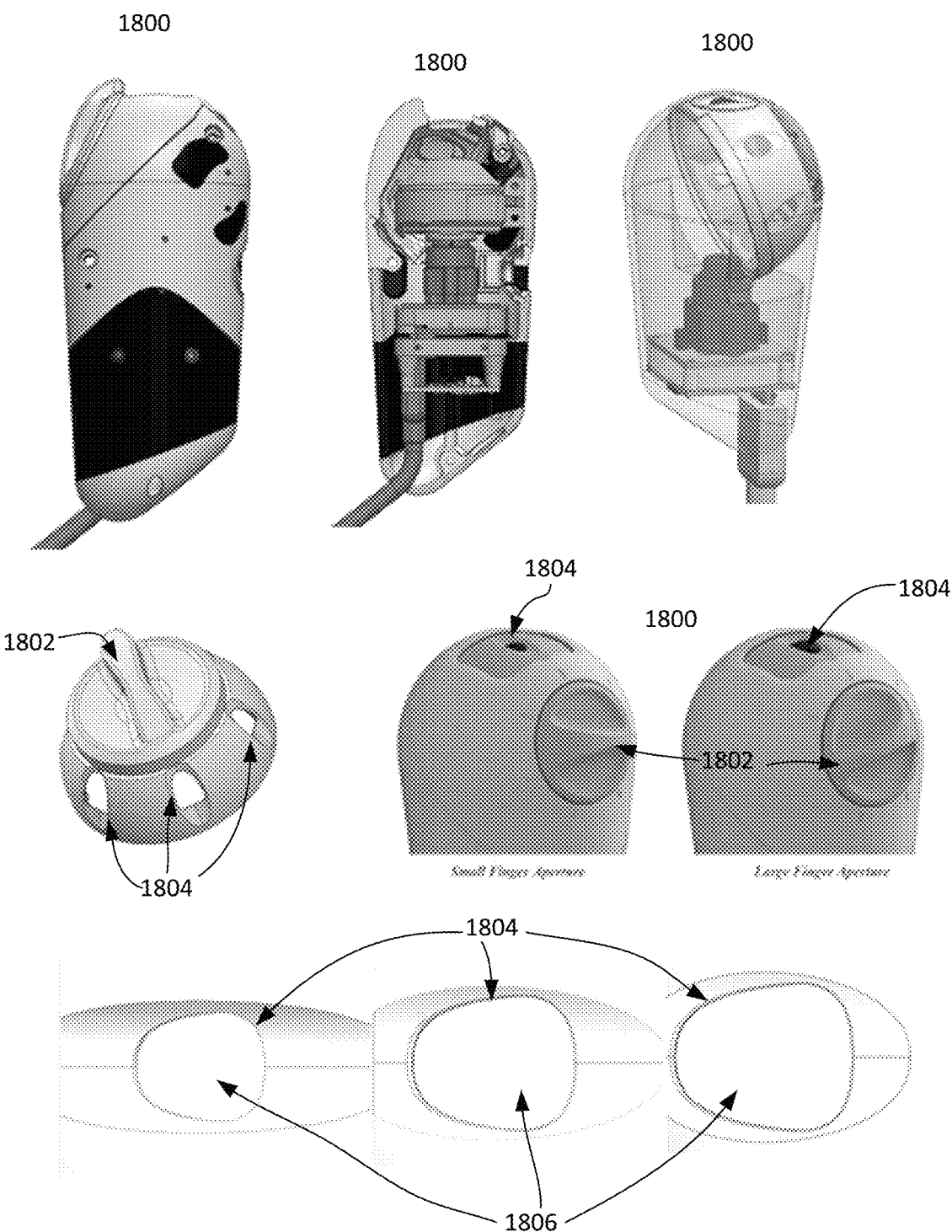
FIG. 18 illustrates an example device that includes an integrated rotary top, in accordance with various embodiments of the present disclosure.

FIG. 18 illustrates example device 1800 that includes an integrated rotary top, in accordance with various embodiments of the present disclosure. The configurable body part support may include a rotary dial 1802 where a number of finger apertures of a variety of sizes and shapes can be selected to match the size and shape of the finger to be imaged. Configurable aperture 1804 may support the fingertip around the edges of the finger while allowing central portion 1806 to be exposed to the illumination light and the camera system. Configurable aperture 1804 may also position the features and body parts such that the imaging system can capture the feature. The size of configurable aperture 1804 can be selected by the operator to match the finger to be imaged. Configurable aperture 1804 may position the finger such that the fingerprint is presented normal to the imaging plane. For example, a single newborn may need five different sized apertures and corresponding configurable body part support, while larger apertures may be used to accommodate larger fingers of children and adults. Configurable aperture 1804 may support a fingertip such that the surface to be imaged is not deformed. The configurable body part support may also help block ambient light. While FIG. 18 illustrates an example device that may be used for fingerprinting, it should be appreciated that the aperture shapes and sizes can also be selected to interrogate other body parts, such as the hand, eye, palm pads, palms, ears, and foot pads.

Figure 2:
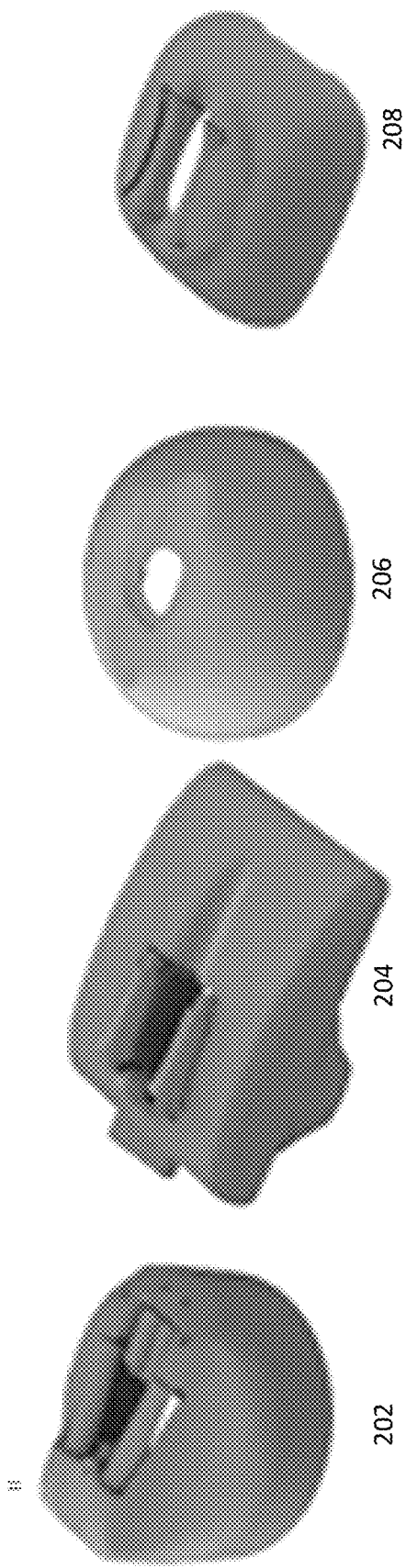
FIG. 2 illustrates multiple interchangeable supports, in accordance with various embodiments of the present disclosure.
Figure 3:
FIG. 3 illustrates an infant using the presently disclosed technology, in accordance with various embodiments of the present disclosure.
Figure 5:
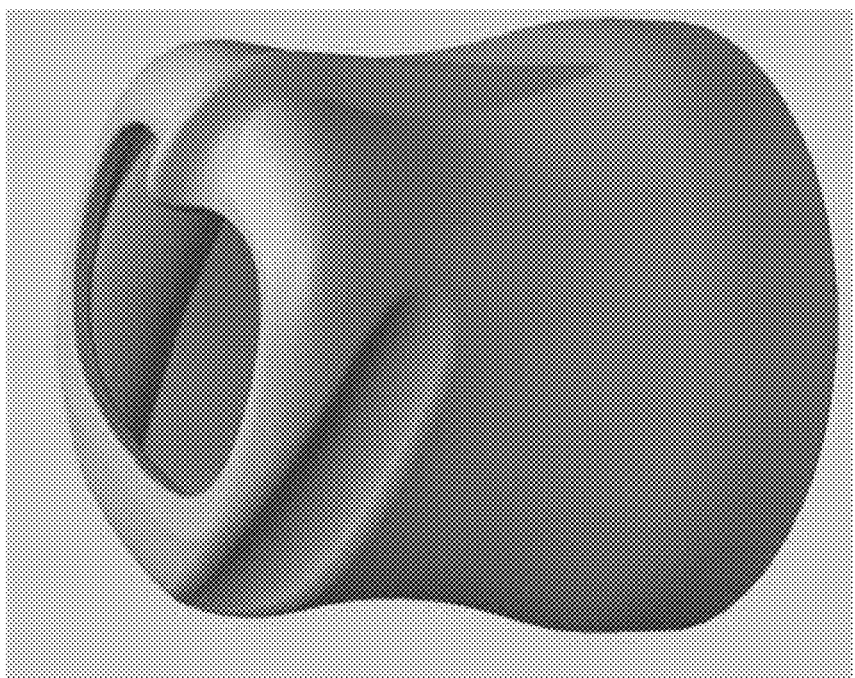
FIG. 5 illustrates features that support placement of the infant hand for palm pad imaging and allow for the hand to grasp the outside of the top, in accordance with various embodiments of the present disclosure.

In embodiments, the multimodal biometric capture device may use interchangeable body part supports. For example, supports can be designed to be removed from the device and replaced with a different size depending upon the needs of the current subject. Various designs may include apertures or rollers to allow for the finger to rotated and get different sides of the fingers. FIGS. 2 and 5 illustrate multiple interchangeable supports, in accordance with various embodiments of the present disclosure. Different sized fingers may be appropriate for different interchangeable supports. 202, 204, and 208 may include rollers to position and rotate a finger. 206 may include support for a finger and an opening in the support to be exposed to the imaging system. The palm attachment in FIG. 5 may illustrate features that support placement of the infant hand for palm pad imaging and allow for the hand to grasp the outside of the top. FIG. 3 illustrates an infant using the presently disclosed technology, in accordance with various embodiments of the present disclosure.

Figure 4:
FIG. 4 illustrates example biometric collections, in accordance with various embodiments of the present disclosure.

In embodiments, there are single finger, multiple finger, palm and palm pad options, along with contact versions and versions that allowed the finger to roll along its axis to obtain all of the fingerprint from edge-to-edge. FIG. 4 illustrates an example of various types of aperture configurations, in accordance with various embodiments of the present disclosure. As illustrated, there are palms, fingers, and a combination of both that are captured.

In addition to the aperture shapes/sizes changing for different finger sizes, the outside shape, or the configurable body part support, of the device can be modified to facilitate proper placement of the fingers/palms, hands, eyes, ears, feet, and other body parts. The palm attachment in FIG. 5 illustrates features that support placement of the infant hand for palm pad imaging and allow for the hand to grasp the outside of the top, in accordance with various embodiments of the present disclosure.

Figure 6:
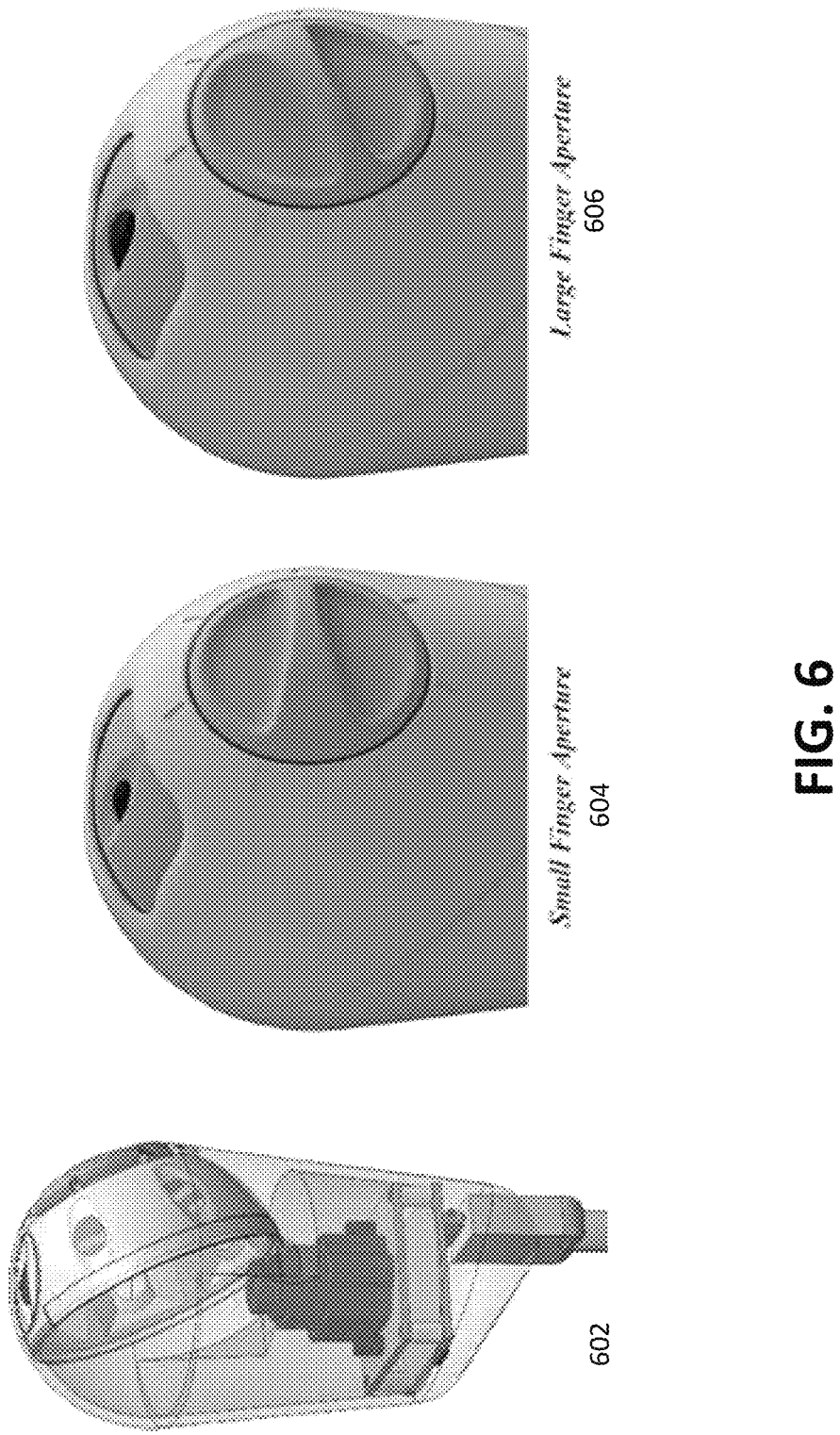
FIG. 6 illustrates different sized supports, in accordance with various embodiments of the present disclosure.

In embodiments, the presently disclosed technology can be designed with a feature that allows for the configurable aperture size to be selected. FIG. 6 illustrates different sized apertures, in accordance with various embodiments of the present disclosure. Gears, embedded assemblies, rotary dials, a linear slide, or other mechanisms in device 602 may be used to change the type of aperture available for use and corresponding configurable body part support. A knob may be able to switch from a small finger aperture 604 to/from a large finger aperture 606. The selectable apertures and corresponding selectable supports may be located on a rotating subassembly such that the proper size can be placed in front of the camera. Each position on the sub-assembly can have different sized apertures for imaging different sized fingers, palms, palm pads, or other biometrics (faces, ears, etc.). Each position on the sub-assembly can be a sized aperture alone, or it can include additional optics to change how the presently disclosed technology operates. For example, a secondary lens may be placed at one of the selectable positions, to allow for imaging of the face for face recognition. This may be used for other biometrics, such as eyes, ears, etc.

Figure 7:
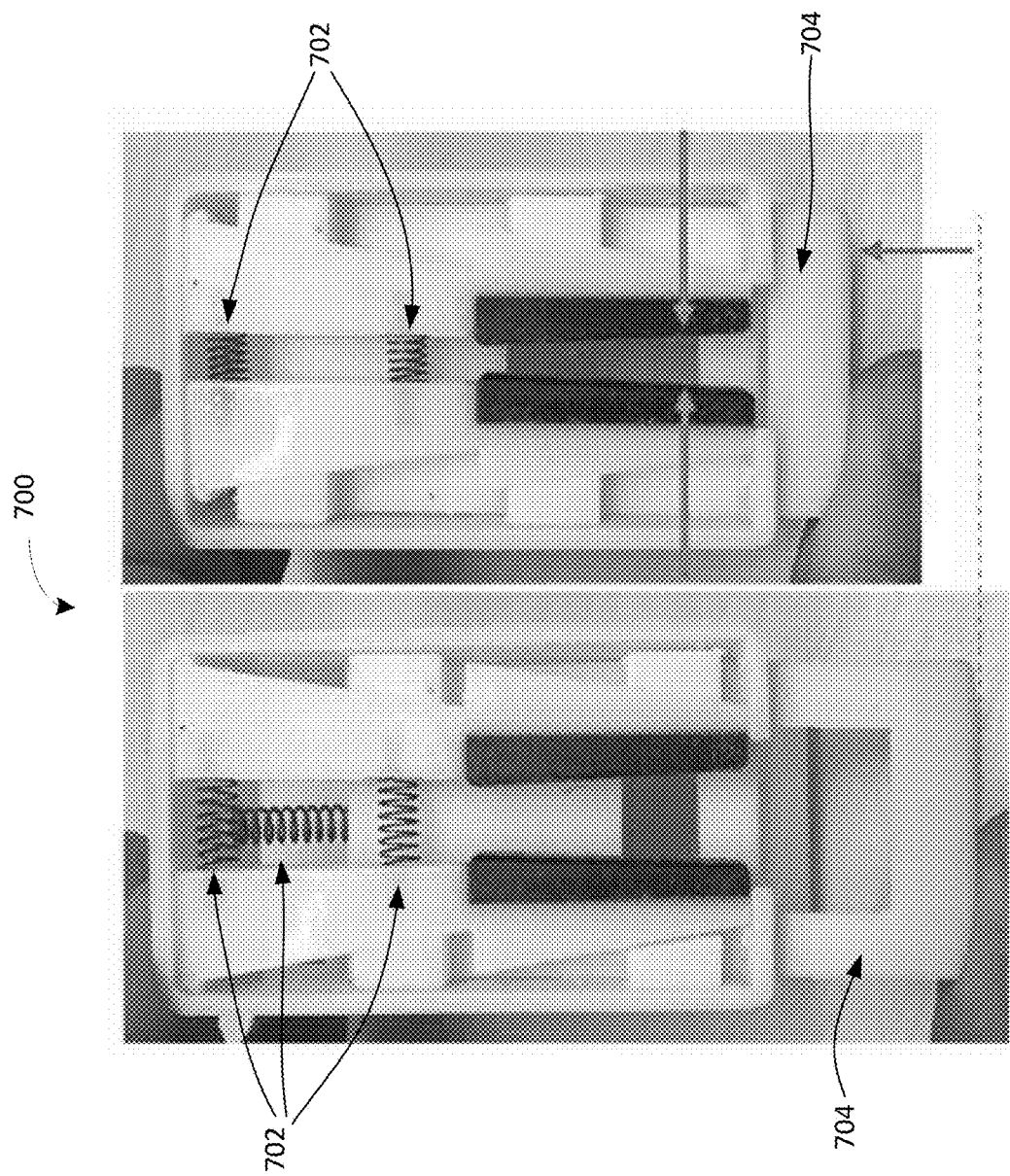
FIG. 7 illustrates an example adjustable aperture that can be adjusted to different finger sizes.

In some embodiments, the configurable aperture can include adjustable sides whose shape and/or position can change to accommodate different finger sizes. FIG. 7 illustrates part of a multimodal biometric capture device where the sides of the configurable aperture 700 can be adjusted to different finger sizes. As illustrated springs 702 may push the sides together and upon pressing a button 704, the sides may move back apart. While embodiments including springs 702 are illustrated, it should be appreciated that other mechanisms may be used to provide adjustable sides (e.g., ball detents, screws, pre-set notches for different-sized and -shaped features, and other mechanisms).

Figure 19:
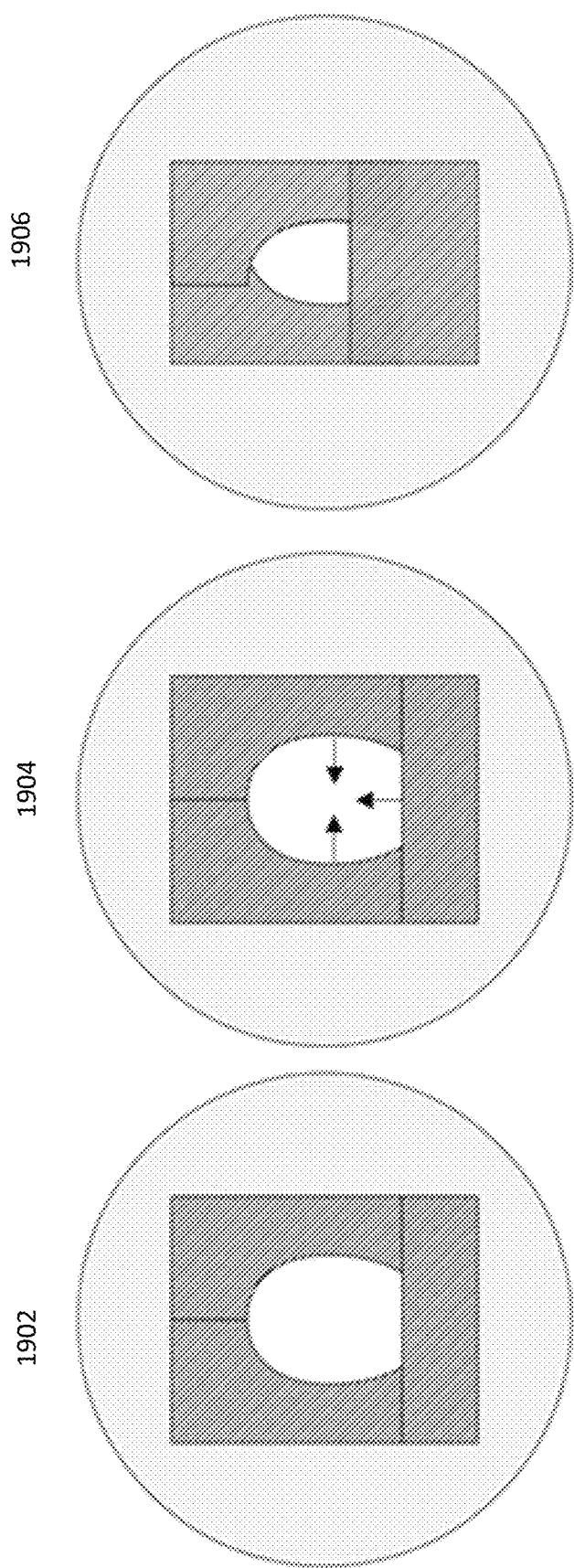
FIG. 19 illustrates an example device including an adjustable aperture, in accordance with various embodiments of the present disclosure.

FIG. 19 illustrates an example device including an adjustable aperture, in accordance with various embodiments of the present disclosure. In some embodiments, the device may include a feature that allows for the aperture size to be selected or adjusted. 1902 may illustrate the adjustable aperture in a first geometry. 1904 may illustrate the adjustable edges of the adjustable aperture to effect the geometry of the adjustable aperture. The sides of aperture can be adjusted to different finger sizes or different portions of different body parts. 1906 may illustrate the adjustable aperture in a second geometry.

Figure 8:
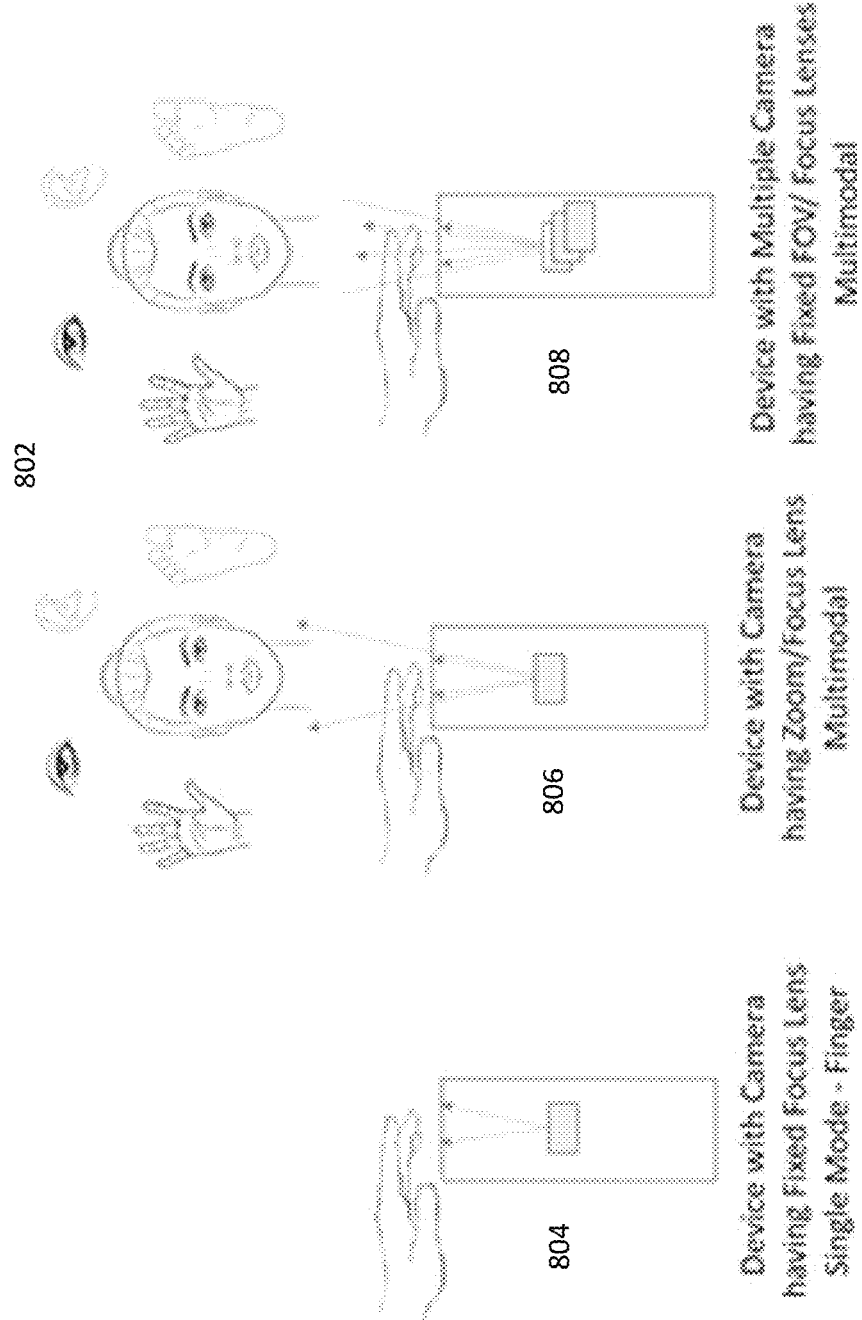
FIG. 8A illustrates example configurations that include one or more cameras in a variety of optical configurations, in accordance with various embodiments of the present disclosure.
FIG. 8B illustrates example configurations that include one or more cameras in a variety of optical configurations, in accordance with various embodiments of the present disclosure.
FIG. 8C illustrates example configurations that include one or more cameras in a variety of optical configurations, in accordance with various embodiments of the present disclosure.

In embodiments, the multimodal biometric capture device may allow for the collection of multiple types of biometrics (simultaneously or at different times), such as the collection of fingerprint, face, ear, palm, iris, and/or retinal scans. FIGS. 8A, 8B, and 8C illustrate a number of possible configurations that include one or more cameras in a variety of optical configurations, in accordance with various embodiments of the present disclosure.

In embodiments, the multimodal biometric capture device may include the capability to collect additional image biometric data. FIG. 8A illustrates an example configuration that allows for the collection of non-contact fingerprint and palm print imagery. This configuration includes a camera 804 with a fixed lens that is focused at a very close distance for imaging fingerprints and/or palm prints and illumination for each body part.

To collect images of other body parts 802 to use as biometrics, a larger stand-off distance may be used to collect a variety of fields of view. The optics for the single camera 806 may include an adjustable zoom/focus so that it could use the same configurable aperture to collect additional biometrics at a variety of working distances and fields of view, as illustrated in FIG. 8B. This could also be accomplished by have the rotatable aperture mechanism contain a position that places a corrective lens into the optical path that would allow for the camera 806 to focus out further to a longer working distance. Thus, there can be a "face" position on the aperture assembly that has an additional optic that can refocus the camera 806 at the farther location to collect another biometric (e.g., a biometric corresponding to the face). In one example, the camera 806 can be used to collect images of the face, ear, palm, iris, and/or retinal scans 802 using camera 806. Camera 806 may include an adjustable zoom and focus lens.

Alternatively, FIG. 8C illustrates that multiple cameras 808 can be used that have fixed lenses that are used independently for the various modes. A single camera may be used for the fingerprint/palm mode, and additional cameras may be used for faces/ears/eyes or any other body part that can be used for identification/verification. In this configuration, the cameras may be tuned to have the color sensitivity, resolution, and field of view appropriate for each of the biometric modes. Each of these modes may incorporate illumination configurations corresponding to the modes all housed in a single device.

Figure 9:
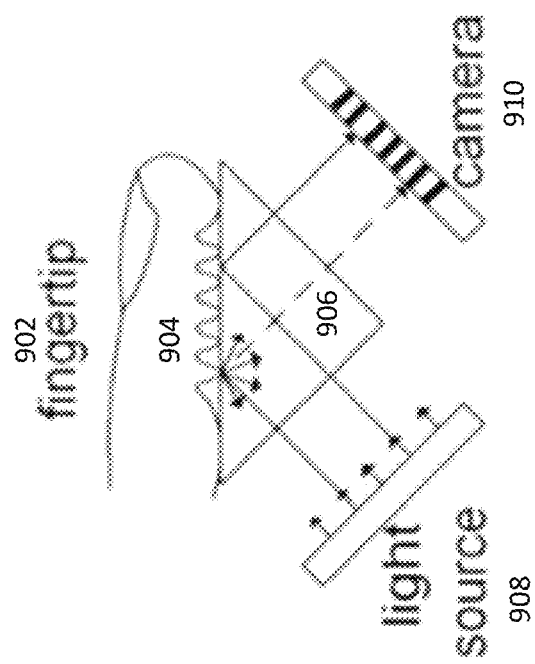
FIG. 9 illustrates an example FTIR configuration.

A method to collect adult fingerprints electronically is to use the optical technique base on FTIR. With FTIR, the finger 902 is placed onto a glass surface 906 that is illuminated with light 908 at a very specific angle, as illustrated in FIG. 9. At locations where there is a fingerprint ridge 904, the light may get absorbed and the digital camera 910 will see a dark area. At locations where there is a valley, the air gap may cause the light 908 to reflect via total internal reflection, and the camera 910 may see a bright area. For infants, however, there are several issues. Upon contact with the glass platen 906, the soft and pliable infant fingerprint will flatten against the surface and the ridges will "squish". Adjacent ridges essentially merge together reducing the air gap to allow the light to reflect to create contrast between the ridges and valleys.

The presently disclosed technology may be able to collect a contact FTIR image and a non-contact image. For example, it may be advantageous to collect a non-contact image of an infant (since contact does not work well on infants) and collect the parent fingerprint using the FTIR technique. The FTIR technique will generate a fingerprint template that may have better interoperability with other biometric/identity systems and databases.

Figure 10B:
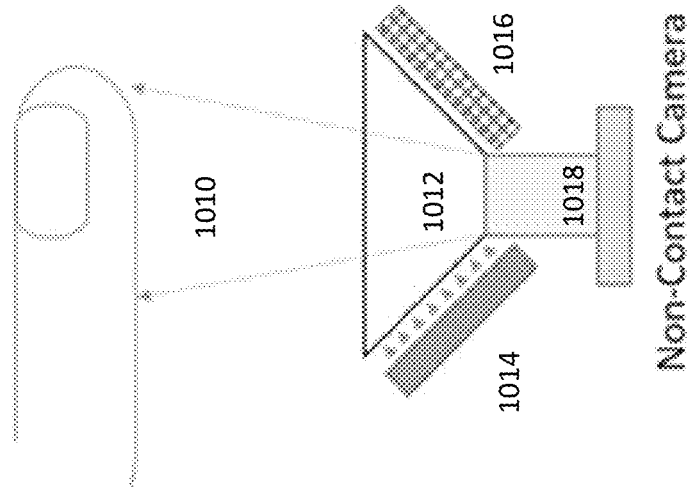
FIG. 10B illustrates a device to collect non-contact images, in accordance with various embodiments of the present disclosure.
Figure 10A:
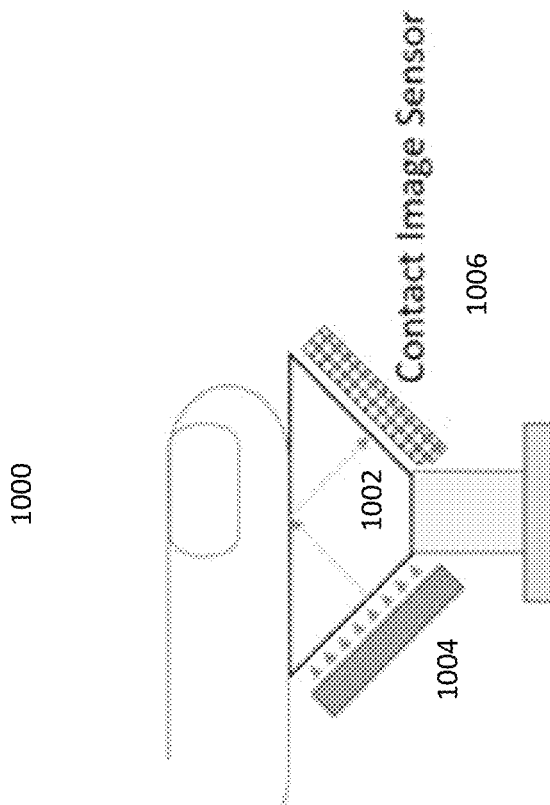
FIG. 10A illustrates a device to collect contact images, in accordance with various embodiments of the present disclosure.

FIG. 10A illustrates device 1000 to collect contact images, in accordance with various embodiments of the present disclosure. As illustrated device 1000 may include camera 1006 that images through the prism 1002. Device 1000 can be used in a contact mode and in a non-contact mode. To image in a non-contact mode, a second camera 1018 may be used that views through the prism (it would effectively act as a window) and image a finger that is not in contact with the prism surface 1012, as illustrated in FIG. 10B. The configuration would have its own light source to illuminate the finger.

Figure 11:
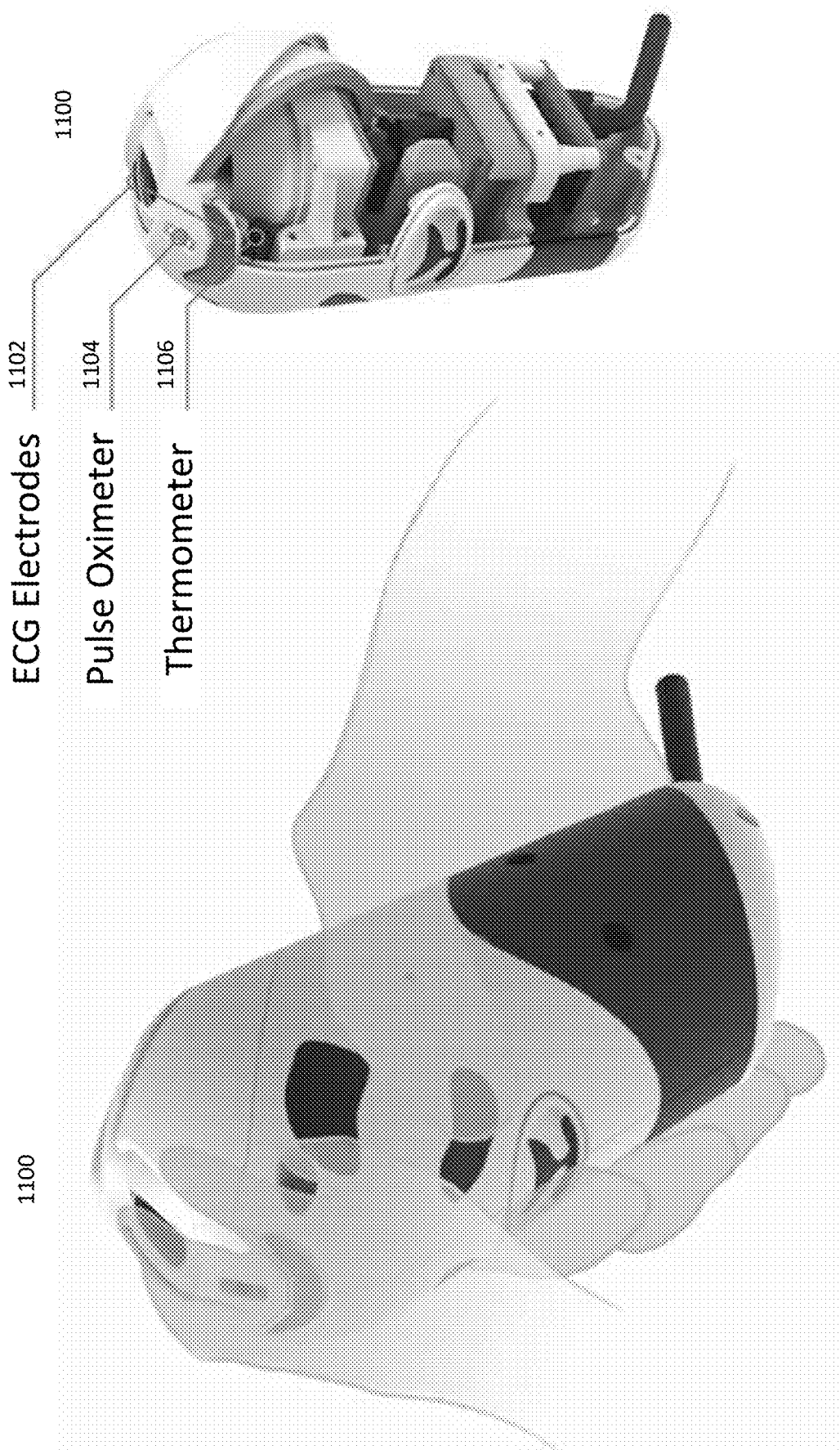
FIG. 11 illustrates an example multimodal biometric capture device, in accordance with various embodiments of the present disclosure.

In embodiments, the multimodal biometric capture device can be configured in any number of ways where the sensors are allowed to interact with the subject's finger/hand, or other body part, to allow for the biometric information to be obtained simultaneously with the collection of the fingerprint, or other feature. FIG. 11 illustrates example multimodal biometric capture device 1100, in accordance with various embodiments of the present disclosure. An example configuration for placement of pulse oximeter 1104, ECG 1102, and thermal sensor 1106 is illustrated. Reflective-type pulse oximeter 1104 is situated under the finger as the finger is placed onto the configurable aperture for scanning. ECG 1102 may include two or more electrodes. For example, one can be incorporated into the configurable aperture and be in contact with the tip of the finger, and the second can be along the side of the device to contact the palm. This provides contact to the subject being printed and allows for several centimeters of distance between the electrodes to achieve an ECG signal. With the pulse oximeter data, blood pressure may also be calculated from these signals. Thermal infrared sensor 1106 may be enclosed under the shell of the device and pointing up towards the configurable aperture. The temperature of the finger can then be measured. Since sensor 1106 is pointing through the configurable aperture, the unit can also be used as a temporal artery temperature probe by pointing the device (without the finger in place) across the forehead of the individual. These readings can be used to determine if the person has a fever, has poor blood oxygenation, has a proper heartbeat, etc., which can be used to determine the subject's health status. In addition, these values can be used to determine other health biometrics, such as, for example, blood pressure. It should be appreciated that additional sensors may be added to determine additional health biometrics or improve the accuracy of the health biometrics. Multimodal biometric capture device 1100 can be configured in any number of ways where the sensors are allowed to interact with the subject's finger/hand to allow for the biometric information to be obtained simultaneously with the collection of the fingerprint. The LEDs and camera can be used to detect heart rate and pulse oxygenation.

Figure 12:
FIG. 12 illustrates example multimodal biometric capture devices, in accordance with various embodiments of the present disclosure.

FIG. 12 illustrates an example device, in accordance with various embodiments of the present disclosure. One device may use interchangeable tops for various size fingers and palms (on left) and the panda device (on the right) may include a rotatable top that has the configurable aperture integrated. The housing for interchangeable apertures may be substantially similar to FIG. 18 above, except it allows except it allows for coupling and decoupling of different tops including different geometries of the apertures to be selected for different finger sizes and interactions. For example, various designs may include apertures or rollers to allow for the finger to rotate and get different sides of the fingers, as shown by FIG. 2. In addition to the aperture shapes/sizes changing for different finger sizes, the outside shape of the device can be modified to facilitate proper placement of the fingers/palms, hands, and other body parts.

Figure 13:
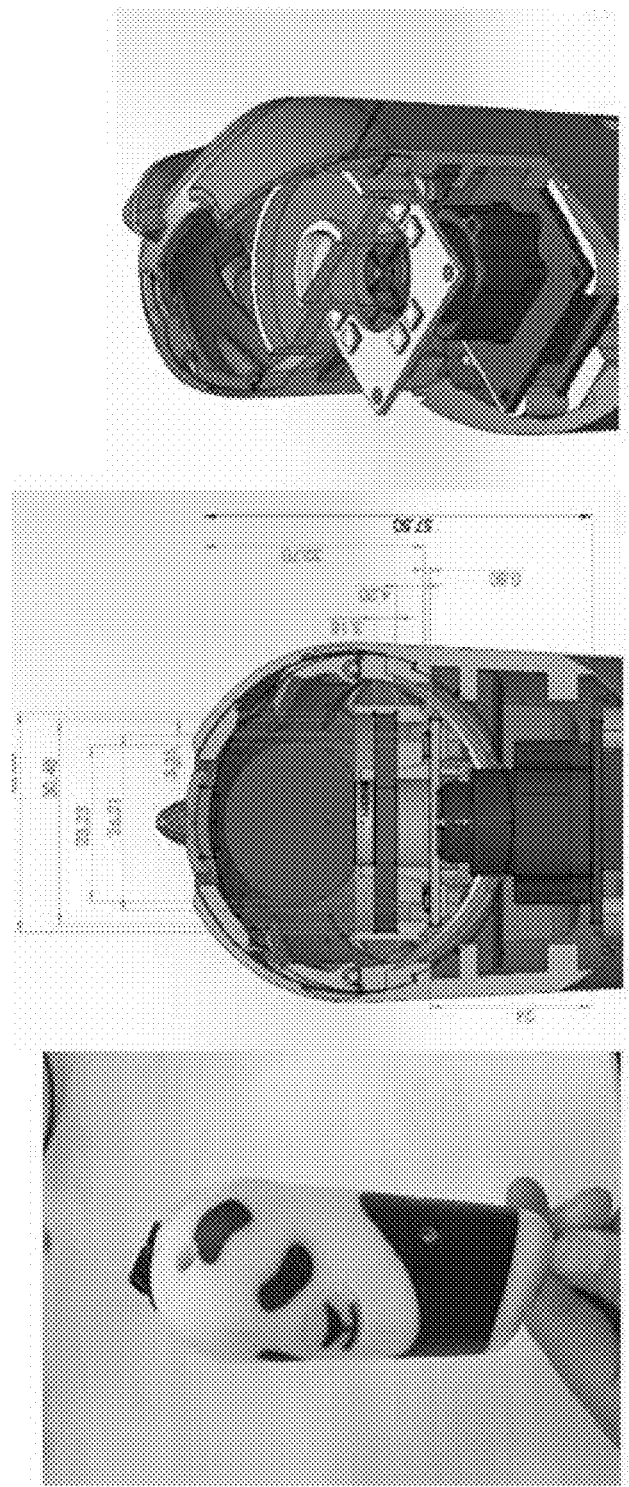
FIG. 13 illustrates example multimodal biometric capture devices, in accordance with various embodiments of the present disclosure.

FIG. 13 illustrates example multimodal biometric capture devices, in accordance with various embodiments of the present disclosure. The middle and right portions of FIG. 13 may be schematics of the example multimodal biometric capture device. The dimensions are an example of how the multimodal biometric capture device may be designed. It should be appreciated that other dimensions may be used for different embodiments.

In some embodiments, the device may include a feature that allows for the aperture size to be selected or adjusted. FIG. 19 illustrates part of a multimodal biometric capture device where the sides of the aperture can be adjusted to different finger sizes.

Figure 20C:
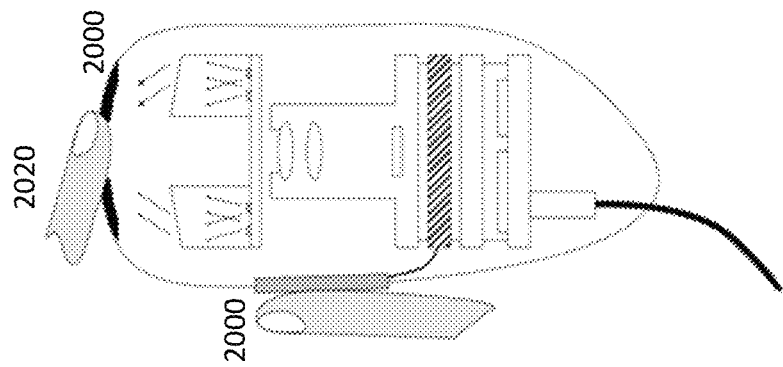
FIG. 20C illustrates an example device comprising a non-contact imaging system and a contact imaging system, in accordance with various embodiments of the present disclosure.

In embodiments, the device may include contact and non-contact methods in a single device or housing. FIG. 20A illustrates example device 2000 comprising a non-contact imaging system, in accordance with various embodiments of the present disclosure. FIG. 20A shows an example prism 2006 being used as a window to allow for the collection of a non-contact image of a finger as previously shown via camera 2008, using dedicated LEDs 2002 and any of the apertures described above. Another light source 2004 may be illustrated but may not be used in non-contact imaging.

Figure 20B:
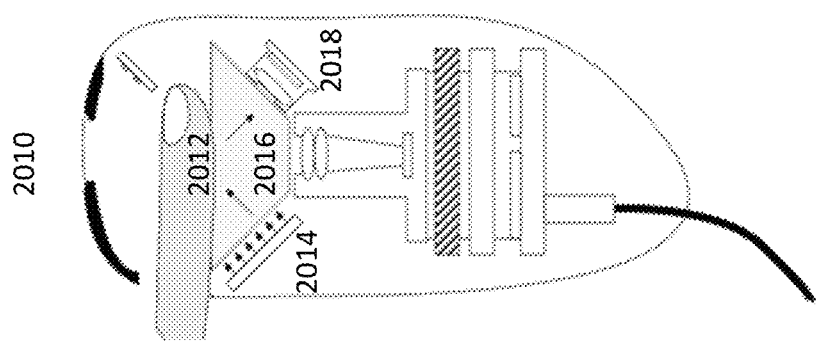
FIG. 20B illustrates an example device comprising a contact imaging system, in accordance with various embodiments of the present disclosure.
Figure 20A:
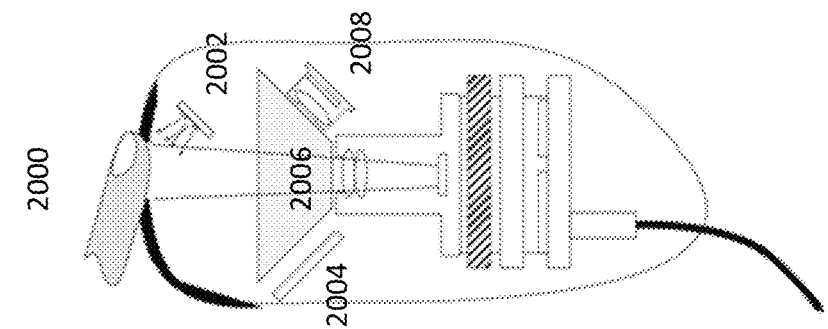
FIG. 20A illustrates an example device comprising a non-contact imaging system, in accordance with various embodiments of the present disclosure.

FIG. 20B illustrates example device 2010 comprising a contact imaging system, in accordance with various embodiments of the present disclosure. FIG. 20B shows how prism 2014 can also be used to collect a fingerprint using FTIR. This technique includes prism 2014 that is illuminated with light source 2016 at a shallow angle to illuminate the contact surface 2012 where the finger is placed to create an FTIR image of the print that is detected using camera 2018 at the exit face of prism 2014. It should be appreciated that FIGS. 20A and 20B may be the same device with a movable top to allow an operator to capture contact and non-contact imaging using a singular imaging system.

FIG. 20C illustrates example device 2020 comprising a non-contact imaging system and a contact imaging system, in accordance with various embodiments of the present disclosure. Contact system 2026 and non-contact system 2024 may be separate systems that are housed in a single device 2020. It should be appreciated that apertures in FIGS. 20A, 20B, and 20C may be substantially similar to the apertures described herein; imaging system 2028 may be substantially similar to the imaging systems described herein; and device 2020 may be substantially similar to devices described herein.

Figure 14:
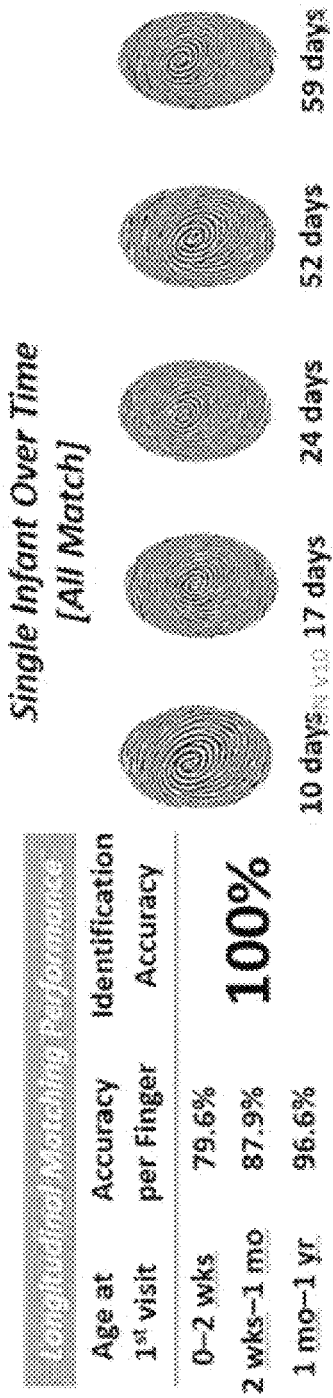
FIG. 14 is a table illustrating matching performance.

FIG. 14 is a table illustrating matching performance. As illustrated, for infants at 0-2 weeks the accuracy per finger was about 79.6%, for infants at 2 wks-1 month have an accuracy per finger of about 87.9%, and for infants at 1 month to about 1 year have an accuracy per finger of about 96.6%. The identification of any infant was 100%.

While fingerprints are illustrated and discussed above, it should be appreciated that other features or portions of body parts, such as an iris, a footprint, a handprint, a palm print, a heart rate, an ear shape, an ear structure, an ear morphology, a body morphology, palm veins, arm veins, footpad veins, finger veins, face physiology, pulse rate, ECG signal, pulse wave morphology, and other features, may be captured by the presently disclosed technology.

The presently disclosed technology may be used in Civil Sectors, for national ID, in health sectors, and in humanitarian sectors. Biometric fingerprint birth registration within 30 days of birth ensures continuity of ID, accurate identification for services and population denominator calculations. Current efforts to obtain digital identity of a country's population may be hindered by an inability to obtain biometrics from children. Most National ID efforts begin at the age of 15, with some able to go down to age 5. There are currently no viable options to obtain fingerprints of children<5 years of age. Rapid ID for routine health care of infants, especially vaccinations, provides for the ability to identify infants for longitudinal health-care follow-up. The presently disclosed technology may also be used with mass vaccinations, public health interventions, crisis triage and tracking, migrants and separated children, proof-of relationship, and human trafficking prevention.

Figure 15:
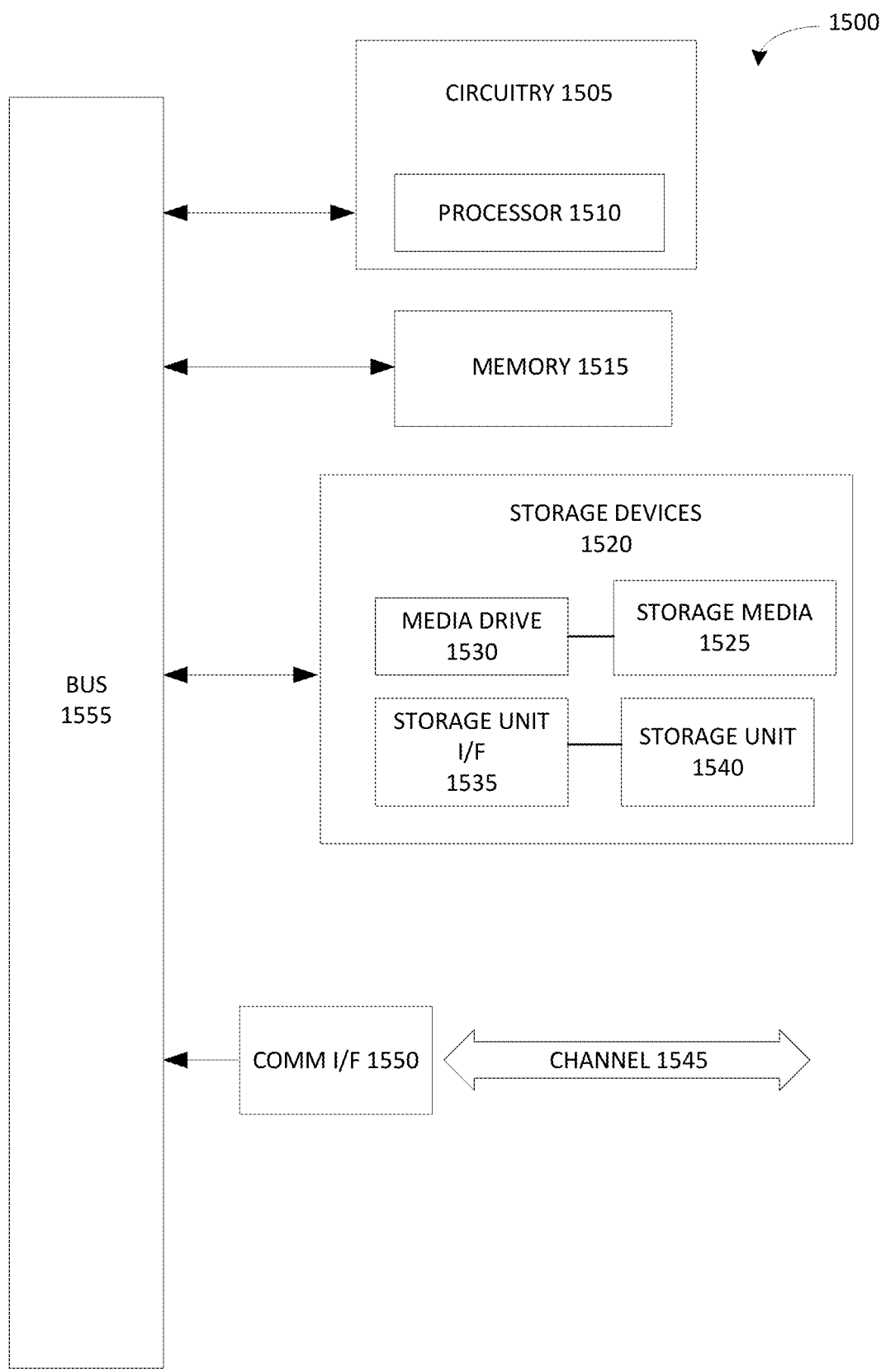
FIG. 15 illustrates an example computing component that may be used to implement features of various embodiments of the disclosure.

FIG. 15 illustrates example computing component 1500, which may in some instances include a processor on a computer system (e.g., control circuit). Computing component 1500 may be used to implement various features and/or functionality of embodiments of the systems, devices, and methods disclosed herein. With regard to the above-described embodiments set forth herein in the context of systems, devices, and methods described with reference to FIGS. 1-12, including embodiments involving the control circuit, one of skill in the art will appreciate additional variations and details regarding the functionality of these embodiments that may be carried out by computing component 1500. In this connection, it will also be appreciated by one of skill in the art upon studying the present disclosure that features and aspects of the various embodiments (e.g., systems) described herein may be implemented with respected to other embodiments (e.g., methods) described herein without departing from the spirit of the disclosure.

As used herein, the term component may describe a given unit of functionality that may be performed in accordance with one or more embodiments of the present application. As used herein, a component may be implemented utilizing any form of hardware, software, or a combination thereof. For example, one or more processors, controllers, ASICs, PLAs, PALs, CPLDs, FPGAs, logical components, software routines, or other mechanisms may be implemented to make up a component. In implementation, the various components described herein may be implemented as discrete components or the functions and features described may be shared in part or in total among one or more components. In other words, as would be apparent to one of ordinary skill in the art after reading this description, the various features and functionality described herein may be implemented in any given application and may be implemented in one or more separate or shared components in various combinations and permutations. Even though various features or elements of functionality may be individually described or claimed as separate components, one of ordinary skill in the art will understand upon studying the present disclosure that these features and functionality may be shared among one or more common software and hardware elements, and such description shall not require or imply that separate hardware or software components are used to implement such features or functionality.

Where components or components of the application are implemented in whole or in part using software, in embodiments, these software elements may be implemented to operate with a computing or processing component capable of carrying out the functionality described with respect thereto. One such example computing component is illustrated in FIG. 15. Various embodiments are described in terms of example computing component 1500. After reading this description, it will become apparent to a person skilled in the relevant art how to implement example configurations described herein using other computing components or architectures.

Referring now to FIG. 15, computing component 1500 may represent, for example, computing or processing capabilities found within mainframes, supercomputers, workstations or servers; desktop, laptop, notebook, or tablet computers; hand-held computing devices (tablets, PDA's, smartphones, cell phones, palmtops, etc.); or the like, depending on the application and/or environment for which computing component 1500 is specifically purposed.

Computing component 1500 may include, for example, one or more processors, controllers, control components, or other processing devices, such as a processor 1510, and such as may be included in circuitry 1505. Processor 1510 may be implemented using a special-purpose processing engine such as, for example, a microprocessor, controller, or other control logic. In the illustrated example, processor 1510 is connected to bus 1555 by way of circuitry 1505, although any communication medium may be used to facilitate interaction with other components of computing component 1500 or to communicate externally.

Computing component 1500 may also include one or more memory components, simply referred to herein as main memory 1515. For example, random access memory (RAM) or other dynamic memory may be used for storing information and instructions to be executed by processor 1510 or circuitry 1505. Main memory 1515 may also be used for storing temporary variables or other intermediate information during execution of instructions to be executed by processor 1510 or circuitry 1505. Computing component 1500 may likewise include a read only memory (ROM) or other static storage device coupled to bus 1555 for storing static information and instructions for processor 1510 or circuitry 1505.

Computing component 1500 may also include one or more various forms of information storage devices 1520, which may include, for example, media drive 1530 and storage unit interface 1535. Media drive 1530 may include a drive or other mechanism to support fixed or removable storage media 1525. For example, a hard disk drive, a floppy disk drive, a magnetic tape drive, an optical disk drive, a CD or DVD drive (R or RW), or other removable or fixed media drive may be provided. Accordingly, removable storage media 1525 may include, for example, a hard disk, a floppy disk, magnetic tape, cartridge, optical disk, a CD or DVD, or other fixed or removable medium that is read by, written to or accessed by media drive 1530. As these examples illustrate, removable storage media 1525 may include a computer usable storage medium having stored therein computer software or data.

In alternative embodiments, information storage devices 1520 may include other similar instrumentalities for allowing computer programs or other instructions or data to be loaded into computing component 1500. Such instrumentalities may include, for example, fixed or removable storage unit 1540 and storage unit interface 1535. Examples of such removable storage units 1540 and storage unit interfaces 1535 may include a program cartridge and cartridge interface, a removable memory (for example, a flash memory or other removable memory component) and memory slot, a PCMCIA slot and card, and other fixed or removable storage units 1540 and storage unit interfaces 1535 that allow software and data to be transferred from removable storage unit 1540 to computing component 1500.

Computing component 1500 may also include a communications interface 1550. Communications interface 1550 may be used to allow software and data to be transferred between computing component 1500 and external devices. Examples of communications interface 1550 include a modem or softmodem, a network interface (such as an Ethernet, network interface card, WiMedia, IEEE 1512.XX, or other interface), a communications port (such as for example, a USB port, IR port, RS232 port Bluetooth® interface, or other port), or other communications interface. Software and data transferred via communications interface 1550 may be carried on signals, which may be electronic, electromagnetic (which includes optical) or other signals capable of being exchanged by a given communications interface 1550. These signals may be provided to/from communications interface 1550 via channel 1545. Channel 1545 may carry signals and may be implemented using a wired or wireless communication medium. Some non-limiting examples of channel 1545 include a phone line, a cellular or other radio link, an RF link, an optical link, a network interface, a local or wide area network, and other wired or wireless communications channels.

In this document, the terms "computer program medium" and "computer usable medium" are used to generally refer to transitory or non-transitory media such as, for example, main memory 1515, storage unit interface 1535, removable storage media 1525, and channel 1545. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions may enable the computing component 1500 or a processor to perform features or functions of the present application as discussed herein.

While various embodiments of the disclosed technology have been described above, it should be understood that they have been presented by way of example, and not of limitation. Likewise, the various diagrams may depict an example architectural or other configuration for the disclosed technology, which is done to aid in understanding the features and functionality that can be included in the disclosed technology. The disclosed technology is not restricted to the illustrated example architectures or configurations, but the desired features can be implemented using a variety of alternative architectures and configurations. It will be apparent to one of skill in the art how alternative functional, logical or physical partitioning and configurations can be implemented to implement the desired features of the technology disclosed herein. Additionally, with regard to flow diagrams, operational descriptions and method claims, the order in which the steps are presented herein shall not mandate that various embodiments be implemented to perform the recited functionality in the same order unless the context dictates otherwise.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. An apparatus comprising:
   a non-contact imaging system, the non-contact imaging system comprising;
      imaging optics;
      optical illumination optically coupled to the imaging optics; and
      a rotary top comprising selectable apertures to support different body parts, each aperture characterized by one or more of a different size and a different shape relative to the other selectable apertures; and
   a housing comprising an opening and coupled to the imaging optics, the optical illumination, and the rotary top;
   wherein the rotary top is configured to rotate to align a selected aperture of the selectable apertures with the opening of the housing.

2. The apparatus of claim 1, wherein one of the different body parts comprises one or more fingers, a palm pad, a palm, and a ball of a foot.

3. The apparatus of claim 1, wherein the housing blocks ambient external light from the non-contact imaging system during imaging of the body part.

4. The apparatus of claim 1, wherein the non-contact imaging system captures images at a resolution of at least 1000 pixels-per-inch.

5. The apparatus of claim 1, wherein the non-contact imaging system comprises one or more cameras.

6. The apparatus of claim 1, wherein the non-contact imaging system comprises one or more of a CMOS and CCD imager, and wherein the non-contact imaging system is monochromatic or color detecting.

7. The apparatus of claim 1, wherein the imaging optics comprises a fixed focus and a fixed focal length or an adjustable focus and an adjustable focal length.

8. The apparatus of claim 1, wherein the optical illumination comprises one or more colors of LEDs over a range of wavelengths from UV through NIR.

9. The apparatus of claim 1, wherein the apparatus further comprises:
   imagers; and
   illumination, wherein the imagers and the illumination collect additional types of biometric images.

10. The apparatus of claim 1, wherein a portion of interest accommodated by a selectable aperture exposes the portion of interest to the imaging optics and the optical illumination to provide non-contact imaging of the portion of interest.

11. The apparatus of claim 1, wherein the apparatus is further configured to measure a health parameter of a subject using the imaging optics and the optical illumination.

12. The apparatus of claim 1, wherein the different body parts comprise fingers of different sizes.

* * * * *